US009107970B2

(12) United States Patent
Morein et al.

(10) Patent No.: US 9,107,970 B2
(45) Date of Patent: Aug. 18, 2015

(54) METHOD AND A FILTER FOR CAPTURING AIRBORNE AGENTS

(76) Inventors: Bror Morein, Uppsala (SE); Göran Friman, Uppsala (SE); Nils-Gunnar Ilbäck, Uppsala (SE)

( * ) Notice: Subject to any disclaimer, the term of this patent is extended or adjusted under 35 U.S.C. 154(b) by 1122 days.

(21) Appl. No.: 12/997,454

(22) PCT Filed: Jul. 13, 2009

(86) PCT No.: PCT/SE2009/000366
§ 371 (c)(1),
(2), (4) Date: Dec. 10, 2010

(87) PCT Pub. No.: WO2010/008336
PCT Pub. Date: Jan. 21, 2010

(65) Prior Publication Data
US 2011/0104197 A1    May 5, 2011

Related U.S. Application Data

(60) Provisional application No. 61/080,729, filed on Jul. 15, 2008.

(51) Int. Cl.
*A61L 9/14* (2006.01)
*A61L 9/16* (2006.01)
(Continued)

(52) U.S. Cl.
CPC ... *A61L 9/14* (2013.01); *A61L 9/16* (2013.01);
(Continued)

(58) Field of Classification Search
CPC ............. A61L 2/00; A61L 2/02; A61L 2/022;
A61L 2/16; A61L 2/22; A61L 9/00; A61L
9/14; A61L 9/145; A61L 2202/00; A61L
2202/10; A61L 2202/11; A61L 2202/12;
A61L 2202/15; A61L 2202/17; A61L
2209/00; A61L 2209/10; A61L 2209/13;
A61L 2209/14; A61L 2209/20; A61L
2209/21; A61L 2209/22; B03C 3/00; B03C
3/34; B03C 3/88; B03C 3/885
USPC .................... 96/43–44, 47; 422/120, 123, 4
See application file for complete search history.

(56) References Cited

U.S. PATENT DOCUMENTS

| 5,855,652 A | 1/1999 | Talley |
| 6,118,040 A | 9/2000 | Coral et al. |

(Continued)

FOREIGN PATENT DOCUMENTS

| CN | 1872396 A | 12/2006 |
| DE | 103 16 759 A1 | 11/2004 |

(Continued)

OTHER PUBLICATIONS

Machine Translation of JP2007-149460 provided by esp@cenet (retrieved Feb. 19, 2014).*

*Primary Examiner* — Sean E Conley
(74) *Attorney, Agent, or Firm* — Dickstein Shapiro LLP

(57) ABSTRACT

A method for capturing airborne agents or products of agents, such as microorganisms, including viruses, and microbial antigens, toxins and allergens, comprising the formation of at least one curtain of charged particles in the form of an emulsion, a suspension or an aerosol, constantly renewing and regenerating said at least one curtain, and passing air containing airborne agents through said at least one curtain, which acting as a filter captures said agents; as well as a particle formulation for performing the method, comprising any charged particles dispersed in a liquid, including lipid-containing particles, e.g. in the form of an emulsion, or micelles, or lipid-containing particles in the form of an aerosol, or any other charged airborne particles in an aerosol.

5 Claims, 3 Drawing Sheets

Figure 1:
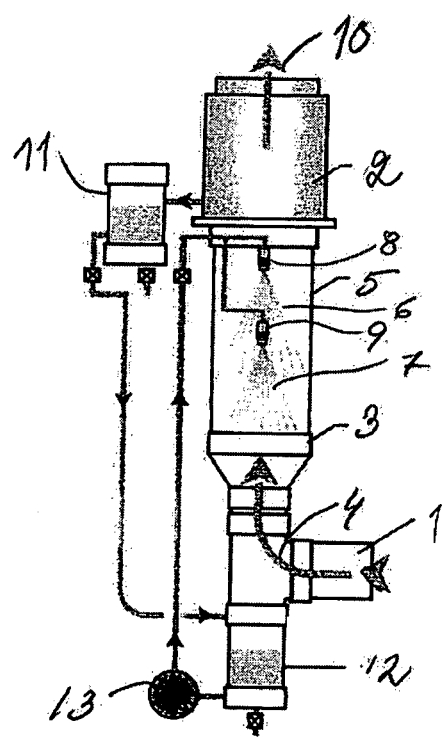

(51) Int. Cl.
  *B01D 47/06* (2006.01)
  *B01D 53/32* (2006.01)
  *A61L 9/18* (2006.01)
  *A61L 9/20* (2006.01)
  *F24F 3/16* (2006.01)

(52) U.S. Cl.
  CPC .............. *B01D 47/06* (2013.01); *B01D 53/323* (2013.01); *A61L 9/18* (2013.01); *A61L 9/20* (2013.01); *B01D 2221/10* (2013.01); *B01D 2247/04* (2013.01); *B01D 2247/101* (2013.01); *B01D 2257/91* (2013.01); *F24F 2003/1682* (2013.01)

(56) References Cited

U.S. PATENT DOCUMENTS

| | | | |
|---|---|---|---|
| 6,231,648 | B1 | 5/2001 | Marlowe |
| 6,287,591 | B1 | 9/2001 | Semple et al. |
| 2003/0079608 | A1 * | 5/2003 | Willey et al. ................... 96/43 |
| 2008/0047281 | A1 | 2/2008 | Fukushima et al. |

FOREIGN PATENT DOCUMENTS

| | | | |
|---|---|---|---|
| EP | 0 280 503 A2 | | 8/1988 |
| JP | 2001-149460 | * | 6/2001 |
| JP | 2006-97960 A1 | | 4/2006 |
| JP | 2007-330898 | * | 12/2007 |

* cited by examiner

METHOD AND A FILTER FOR CAPTURING AIRBORNE AGENTS

This application claims the benefit of U.S. Provisional Application Ser. No. 61/080,729, filed on Jul. 15, 2008.

FIELD OF INVENTION

The present invention relates to a method and a filter for capturing airborne agents, such as microorganisms, including viruses, and microbial antigens, as well as toxins and allergens and other harmful molecules.

BACKGROUND

An increasing problem of airborne microorganisms, including viruses (e.g. influenza and SARS), as well as of microbial and other antigens and toxins, resulting in increased morbidity and mortality due to aggressive viruses, resistant bacteria and sensitivity to allergens and toxins, requires an efficient method to remove these agents and molecules from contaminated air of various environments and premises. The latter include environments with conventional air filters, such as hospital operating theatres and hospital ward rooms, e.g. ward rooms for severely immuno suppressed patients. In modern hospitals, an increasing number of patients are receiving immunosuppressive therapy for cancer and other serious diseases making them highly sensitive to a variety of infectious agents, while patients who have been struck by highly contagious agents are treated in infectious disease isolation wards that are commonly situated within the same hospital buildings. Also, other environments where presently no air filters are in common use, including day care centres, kindergartens and schools, especially for small children, air-borne microorganisms (e.g. penicillin-resistant pneumococci causing middle ear inflammation and pneumonia) may pose a threat, and such environments would thus benefit from air-cleaning measures. Furthermore, premises used in the globally fast growing poultry industry and other food production require efficient removal of viruses and bacteria from air to reduce the risk of microbial contamination and exchange of organisms that may undergo genetic recombination potentially resulting in epidemic outbreaks of serious infections, such as the bird and swine flu. Also, in transportation vehicles, including airplanes, conventional air conditioning equipment may carry microorganisms from one infected passenger to other passengers.

Conventional mesh network air filters have limited capacity to capture small bacteria, viruses and components of microorganisms, as well as molecules like allergens and toxins. The most advanced conventional filter system is the High Efficiency Particulate Air (HEPA) filter which is preferably used for cleaning the air in high risk laboratories. One disadvantage with mesh network filters is their inherent inability to kill infectious agents that may have been caught by the filter. Another disadvantage is that they get clogged and become inefficient after variable periods of time and then can potentially start leaking because of the high air pressure that is then required to overcome the filter resistance. Notably, bound infectious microorganisms may then detach and pose a risk to individuals in the environment.

Today there are patents or patent applications on conventional filters based on mesh networks with the capacity to clean the air from microorganisms, including patent applications based on capturing microorganisms by electrostatic binding. The above mentioned drawback with mesh network filters, including HEPA-filters, with their gradual clogging leads to increasing air resistance and decreasing filtering efficiency over time. These insufficiencies, which are difficult to detect and control, pose a risk despite the fact HEPA-filters are usually regularly exchanged over time. Moreover, the exchange procedure of mesh network filters, including HEPA-filters, is in itself connected with a certain risk of spreading infectious microorganisms stuck in the filter. Finally, HEPA filters are generally expensive and require efficient pre-filtering systems.

Because of the increasing air traffic between countries and continents this mode of transmission of microorganisms will have to be taken seriously. Finally, the global climate changes that are thought to take place will most likely affect the disease panorama in many parts of the world and, among other things, result in increased demand for efficient removal of viruses and other microorganisms, as well as allergens and toxins, from air.

Accordingly there is an increasing need for a new technique for taking care of the problems with airborne harmful agents.

SUMMARY OF THE INVENTION

The object of the present invention is to provide a method and a particle formulation for capturing airborne agents which solves the problems associated with the prior art and meet future demands of capturing airborne microorganisms.

This and other objects are obtained with the method as defined in claim 1 and the particle formulation as defined in claim 3.

Further developments and preferred embodiments of the invention are defined in the sub claims.

The present invention overcomes the mentioned problems of conventional filters based on solid three dimensional networks by the construction of a fluid or aerosol filter in the form of a curtain of particles/droplets, or micelles that is constantly being renewed, regenerated and with the possibility to be continuously decontaminated. There is no limitation in the number of layers (curtains) that can be established in the construction to capture microorganisms or toxic etc. molecules and no limit to minimise the space between the particles/droplets or micelles that are designed to capture the microorganisms/molecules An added value of the present invention is the possibility to kill the captured microorganisms, including viruses, and inactivate captured antigens, toxins and allergens. The invention encompasses the formation of a fluid or aerosol filter consisting of charged particles, or micelles, in a liquid or dry phase.

The particles can be any charged particles dispersed in liquid, or dry particles, including lipid-containing particles e.g. in the form of an emulsion, or micelles in a liquid solution. The lipid-containing particle, or micelle, exists in a liquid or aerosol phase with a lipophilic nucleus surrounded by amphipatic molecules with an external polar part, which can be positively and/or negatively charged and thus capture airborne agents and molecules with the opposite charge.

In the case of lipid containing particles, the emulsion particle has a lipophilic nucleus that can be stabilised by stabilising molecules with a prominent lipophilic part incorporated into the nucleus and a less prominent external polar part. The molecule devised for capturing has a prominent charged region extended outward and a minor lipophilic region anchoring the molecule in the lipophilic center. Another suitable particle formulation is the micelle built up by amphiphatic molecules with the lipophilic region in the centre and the polar charged region extended outwards in the water phase. Thus, the invention is not based on solid three dimensional filter meshes but on a fluid or aerosol filter with a curtain of charged particles, for instance lipid-containing particles or micelles, which capture airborne agents by electrostatic binding, with or without the supportive affinity binding. Affinity binding may be based on lectin binding or lipophilic interaction and/or any other affinity binding, where, optionally after capture, the microorganisms, including viruses, can be killed and antigens, toxins, allergens and other captured molecules rendered harmless by inactivating additives.

The particle filter encompasses a fluid filter of particles or an aerosol of particles. It may consist of a water solution or any other solution or suspension that harbours the particles or the particles can be dry and form an aerosol; for instance, it can be a salt solution not eluting the captured agents from the filter particles, i.e. with a suitably low ionic composition. Alternatively, it can be an emulsion of lipid-containing particles, or micelles, or an aerosol of dry particles.

The solution-suspension-emulsion-aerosol, respectively, can contain additives that kill any type of captured microorganisms, for example pH-, oxidative-, or other disinfectant-based killing, and/or additives that make captured antigens, toxins and allergens and other captured molecules innocent.

The fluid or aerosol filter according to the invention is not impaired by the afore-mentioned limitations and risks associated with mesh network filters and can be produced and maintained at a lower cost than the HEPA filter.

In conclusion, the filtering principle according to the invention is not based on size filtering as e.g. in HEPA filters according to the prior art, but is instead based on attraction according to specific characteristics of the agents to be captured. The new concept of a fluid or aerosol filter fills an unmet need of capturing both small microorganisms like viruses and molecules like allergens and toxins, as well as radioactive and other harmful molecules. The microorganisms are captured regardless of whether they exist as freely airborne particles, or exist in water droplets, or are coupled to small tissue fragments usually originating in the airways or gastrointestinal or urinary systems or skin or fur or feathers of man or animals. In addition, the invention facilitates the killing/inactivation of the captured agents. Thus, the fluid or aerosol filter according to the invention will be efficient in an environment with a broad size panorama of air contaminants.

SHORT DESCRIPTION OF THE DRAWINGS

Figure 2:
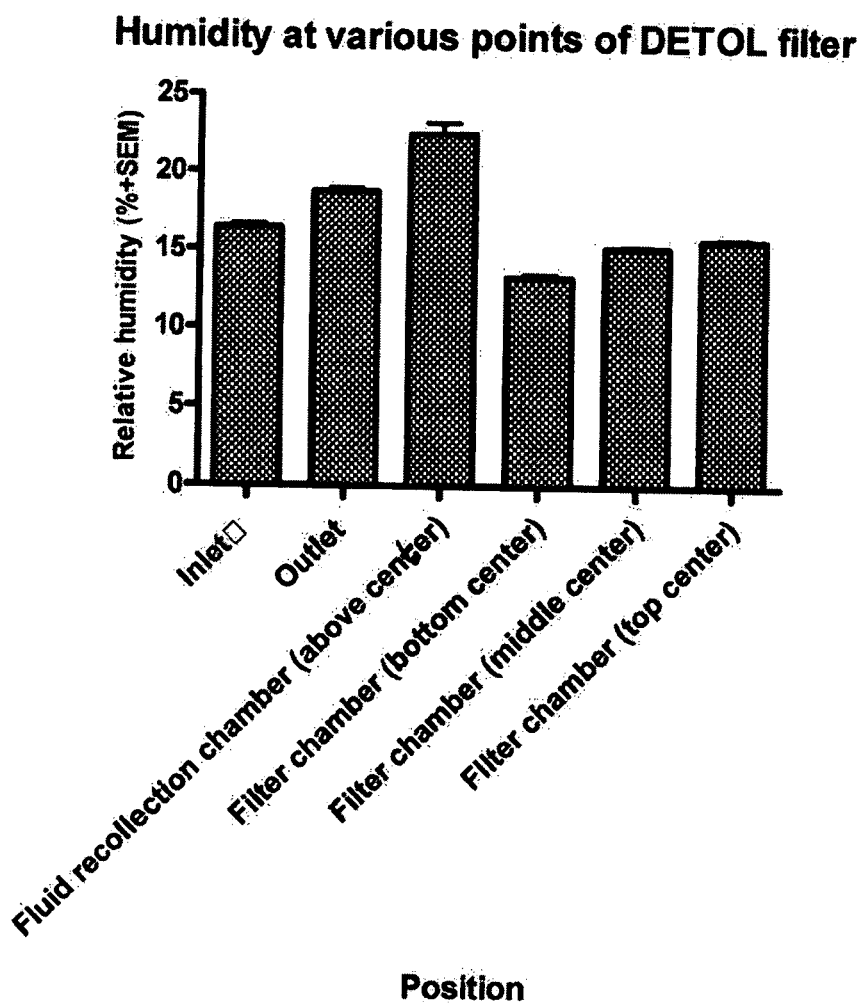
Figure 3:
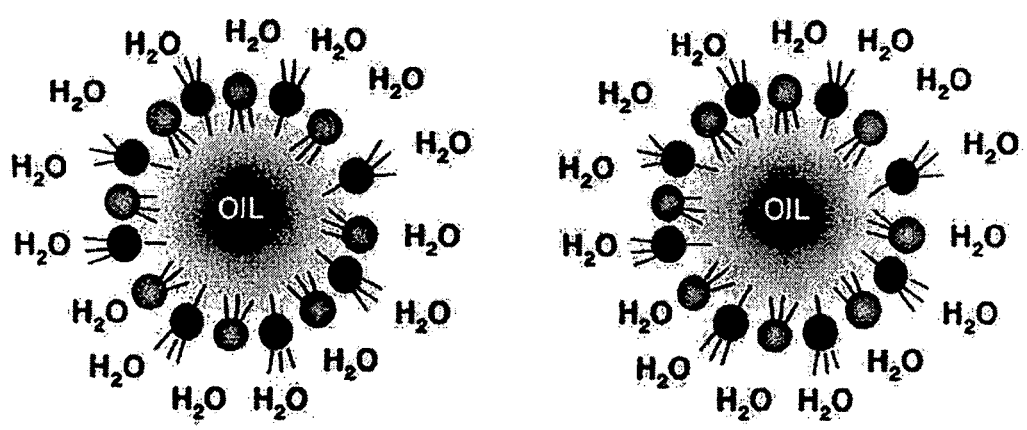

The invention will be described in more detail in the following description of embodiments of the invention, and with reference to the accompanying drawings, on which FIG. 1 is a schematic view of a fluid or aerosol filter system according to the present invention;

FIG. 2 is a staple diagram showing the humidity at various points in the filter working according to the invention; and FIG. 3 shows an example of a lipid/oil particle according to the invention.

DETAILED DESCRIPTION OF THE INVENTION

The present invention relates to a new concept and technique for capturing airborne microbes, including viruses, and microbial antigens, toxins and allergens. Our invention is not based on solid filter meshes but on a fluid or aerosol filter with a curtain of charged particles that attract and capture airborne agents by electrostatic binding and secondary lipophilic and/or other affinity binding, e.g. lectin binding where, after capture, the microorganisms can be killed and antigens, toxins and allergens rendered harmless by inactivating additives, in the following referred to as the DETOL fluid or aerosol filter. Only a minimal air pressure is required for pumping or sucking the air to be cleaned through the DETOL fluid or aerosol filter. There are several commercially available charged particles that can be used for proof of concept of the DETOL fluid or aerosol filter. For the development of an optimal future charged particle, latex particles and dextran particles have been tested and evaluated in the DETOL fluid and aerosol filter system. Based on these results it can be concluded that lipid/oil particles with a lipophilic nucleus surrounded by amphipatic molecules with an external polar part, which can be positively and/or negatively charged, may also serve the purpose of the DETOL fluid or aerosol filter. The DETOL fluid or aerosol filter concept is unique, and such constructions for capturing agents, with the possibility of killing microorganisms, including viruses, can not be found in the scientific and technical literature or among patents or patent applications.

In FIG. 1 a schematic view illustrates the principles of the DETOL fluid or aerosol filter. Air to be cleaned sucked is into the system through the inlet 1 by a cyclone 2 placed on top of the equipment. The incoming air first passes through a device 3 to generate suitable turbulence of the air flow, the air flow being shown with a fat arrow 4. In the central chamber 5, the air interacts with curtains 6, 7 of charged particles in liquid or aerosol formed by nozzles 8, 9 capturing microorganisms, toxins and molecules etc in the air by electrostatic force optionally supplemented by lipophilic or other affinity binding. The cleaned air passes through the cyclone 2 and exits at the outlet 10. The cyclone also acts as an extra security device separating particles accidentally reaching that far. The particles collected by the centrifuge enters a fluid collector 11, move down to a lower chamber 12 for collecting fluid and particles to be regenerated and recirculated into the DETOL fluid or aerosol filter. A pump 13 serves to circulate fluid and particles in the system.

The charged particle, or micelle, optionally contains a lipophilic structure-component, facilitating lipophilic interactions and binding serving as a supplement to the electrostatic binding. The lipophilic nucleus can be stabilised by stabilising molecules with a prominent lipophilic part incorporated into the nucleus and a less prominent external polar part. The different types of particles can optionally be stabilised by cross-linking. One example of a lipid/oil particle is described in FIG. 3.

By keeping the charged particles in an environment with a z-potential of more than +30 mV or less than −30 mV, it is well known that the particles are kept dispersed and do not aggregate.

Lipophilic interactions offer additional binding and also one manner of inactivation of agents surrounded by a lipid membrane, including many viruses, i.e., facilitate membrane lysis and damage lipid membranes by blebbing. The particles can virtually be made in any sizes (such as from 10 nm to 100 μm) and can, but not limited to, be built by a technique where an oil/lipid nucleus is stabilized by an amphipatic stabilization molecule or assembled as a micelle. In this complex another amphipatic molecule is incorporated into the lipophilic nucleus, with a prominent polar part (positively or negatively charged), facing outwards and optionally harbouring an affinity group. This external part has the function of binding agents, such as viruses, other microorganisms, products of microorganisms, other antigens, toxins, allergens, etc. that are all either negatively or positively charged. Charged particles suitable for the DETOL fluid or aerosol filter can be constructed with specified properties for capturing the specified or non-specified agents or molecules with positive, negative or both charges, and with different affinity bindings, for instance lecithin-carbohydrate interactions. Optionally, the charged particles in the fluid phase can contain a chelating agent, an archaeosom-particle based on polar ether lipids, chocoleate, polymers (e.g. polylactide coglycolide particle), chitosan cat ionic polysaccharide—chitosan polymers—microspheres, polyalginate with coating, e.g. poly-1-lysine, giving positive surface charge and increased stability.

In the DETOL fluid or aerosol filter, particles will be used, either suspended in liquid, or as dry particles in aerosol. For the construction of charged lipid/oil particles, emulsion techniques will be used because: 1. emulsions can be made with different specifications; 2. techniques for producing various emulsions are available; 3. emulsion particles can be made with desired/suitable size; 4. emulsions can be produced at an commercially attractive cost; 5. production can easily be scaled up to large volumes; 6. emulsions can be made biologically degradable, which is an environmental advantage; and 7. various active components can be incorporated in emulsion particles. Within the vaccine industry stable particles have been developed using the emulsion technique, e.g. oil/water emulsions with low viscosity similar to water can be made, which is required for a fluid filter.

Formulation of charged lipid/oil particles in emulsion can be made by well-known technology, for example by the "jet breakup method" (R. N. Berglund and B. Y. H. Liu, Environ. Sci. Technol. 7, 147 (1973)). A suspension of these particles can be created by using high pressure and high speed spraying of oil together with amphipatic molecules through nozzles. The materials to be used for the creation of the emulsions include, for example, surfactants soluble in oil, such as Span 85 (stabilization of the emulsion particles), surfactants soluble in water, such as Tween 80 (negatively charged), and CTAC8 and CAT16 (positively charged), polar lipids, for example from Archea bacteria (positively charged). In addition, other commercially attractive lipids, such as soy bean oil, peanut oil, and squalene, could alternatively be used for the creation of suitably charged particles for the DETOL fluid or aerosol filter.

Air to be decontaminated is pumped into a cylinder and through the liquid curtain of the DETOL fluid or aerosol filter. The liquid or aerosol curtain of the DETOL fluid or aerosol filter is uninterruptedly created by nozzles connected to the cylinder where the curtain completely covers its inner diameter. The curtain can be conical or have a more flat shape. The equipment used can create one, or a series, of liquid or aerosol curtains containing charged particles with various properties, for example in size and charge. Briefly, the liquid curtain is generated by pressing the particle-containing liquid through nozzles into the cylinder. Alternatively, dry particles are pressed through the nozzles thus creating an aerosol curtain. The passage of the air to be cleaned through the filter chamber can be brought about, either by creating a positive air pressure at the inlet, or by creating a negative air pressure by the action of a cyclone at the outlet, although not limited to a cyclone. Air to be decontaminated is guided into the cylinder, where it has to pass through the liquid curtains, or curtains of dry particles, where agents and molecules to be removed are captured by the charged particles. In the series of DETOL fluid or aerosol filter curtains, each curtain can be tailored for a required purpose, e.g. for rough contaminants, positively charged toxins or allergens or negatively charged microorganisms or other agents. The continuously generated liquid or aerosol curtain of charged particles with the captured agents and molecules flow down the inside of the cylinder down into a recollection chamber at the bottom of the cylinder where captured agents and molecules are detached and inactivated by additives (12, FIG. 1). Optionally these particles with their captured agents and molecules pass through a cyclone (2, FIG. 1), where remaining particles with their captured agents and molecules are separated from the purified air. After removal of these remaining charged particles with their captured agents and molecules by the cyclone they will pass into the afore-mentioned recollection chamber, where captured agents and molecules are detached and inactivated by additives. Then the charged lipid/oil particles, or micelles, are optionally disintegrated into their subcomponents to be used for regeneration of new particles that are re-circulated etc. Optionally, the particles are not disintegrated but re-used in their original form but decontaminated before re-use. Thus, the equipment can be constructed so that de novo liquid or aerosol curtains with charged particles in the DETOL fluid or aerosol filter are continuously generated. The equipment can be supplied with two or more collection/recollection chambers connected to be used alternatively when one chamber is regenerated or exchanged.

Recirculated charged particles with captured agents and molecules can be exposed to various microorganism-killing procedures, for example, halogenated and chlorine-containing substances, UV irradiation, heating, microwaves, opsonising, aluminium and silver salts, metal ions (e.g. silver, copper, zinc, mercury, titanium, nickel and cobalt). Furthermore, metal ions could potentially be built into the charged particles. Notably, magnetic ions, including iron, nickel, cobalt etc. can be incorporated into the charged particles to enable magnetic separation in the recollection chamber and subsequent destruction of captured agents and molecules. Then particles can be regenerated and re-used in the DETOL fluid or aerosol filter system.

Test and analysis systems are available on the market or can readily be constructed making it possible to determine and measure the following: the amount of virus particles that is fed into the DETOL fluid or aerosol filter system; the amount that is captured by the charged particle curtain of the DETOL fluid or aerosol filter; and the amount possibly passing through the DETOL fluid or aerosol filter system without being captured.

Under the normal working conditions, relative humidity (% rh) at various positions within the DETOL fluid or aerosol filter were measured with VelociCalc 9555 multi-function ventilation meter, i.e. at the inlet, the outlet and through holes above the fluid recollection chamber as well as 3 points within the filter chamber. This is illustrated in FIG. 2 in the form of a staple diagram, where the different positions in the plant are marked on the x-axis and the relative humidity on the y-axis.

An oil-in-water (o/w) emulsion used in the tests was visible as milky fluid. The density was 0.9963 g/ml; the particle size was approx. 165 nm and stable; the electrostatic charge was >+30 or <−30 mv, which prevents aggregation; the viscosity was comparable to that of water; and the composition 0.5% Tween 80 water soluble "surfactant" $H_2O$ ●; 0.5% Span 85 oil soluble "surfactant" (stabilizator) ○; 4.5% squalen oil; 10 nM Na-citrate buffer to keep stable pH and Z-potential. The particle is illustrated in FIG. 3.

Embodiments of the Invention

The invention is not based on filter meshes but on a fluid or aerosol filter with a curtain of charged particles that capture airborne agents by electrostatic binding supplemented by lipophilic and any other affinity binding, where, after capture, the microorganisms can be killed and antigens, toxins and allergens and other harmful or potentially harmful molecules rendered harmless by inactivating additives.

The particles in the DETOL fluid or aerosol filter are efficient and versatile particles or, in other words, particulate molecular constructions from nanosize to microsize with the capacity of capturing viruses and other microorganisms, including bacteria, fungi and parasites. Also, substances, antigens, toxins and allergens, whether produced by microorganisms or not, and other harmful molecules are captured.

There are several commercially available charged particles that can be used for proof of concept of the DETOL fluid or aerosol filter. For the development of an optimal future charged particle latex particles and agarose particles have been tested and evaluated in the DETOL fluid or aerosol filter. It should be noted that the particles must not be sticky because this would cause aggregation.

Materials and Methods

A. Fluid or Aerosol Filter—Technical Equipment

Air to be decontaminated is pumped or sucked into a cylinder and through a liquid or aerosol curtain of charged particles (FIG. 1). The liquid curtain of charged particles is uninterruptedly created by nozzles connected to the cylinder where the curtain completely covers its inner diameter. Air to be decontaminated is guided into the cylinder, where it has to pass through the liquid or aerosol curtains where agents to be removed are captured by the charged particles.

B. Electrostatically Charged Cellulose Filter Networks

1. Corona virus labelled with [$^{35}$S]-methionine/cysteine was used to test its binding (adsorption) to non-treated cellulose filters and cellulose filters treated with Quab ($CIC_{18}H_{36}NH_2$) a hydrocarbon chain containing a positively charged aminogroup. Pieces of non-treated and Quab treated filters with a surface area of about 0.5 cm$^2$ were dipped into a suspension of virus in water for about 1 minute and then washed efficiently twice with de-ionized water.

2. This charged Quab filter was also tested with airborne viruses, i.e. the virus in water in a chamber for aerosol generation was connected to an air-bomb and the calibrated air-pressure was adjusted to 2.2 bar, representing the normal physiological inhalation of 7 liters per minute. This aerosol was allowed to pass through a single layer of the cellulose network.

C. Particles

The charged particles in the DETOL fluid or aerosol filter are efficient and versatile particles or, in other words, particulate molecular constructions, or micelles, from nanosize to microsize with the capacity of capturing viruses and other microorganisms, including bacteria, fungi and parasites. Also substances, toxins and allergens, whether produced by microorganisms or not, and other harmful or potentially harmful molecules are captured.

Corona virus labelled with [$^{35}$S]-methionine/cysteine was used to test its binding (adsorption) to four types of commercially available and electrostatic charged latex microspheres (beads) with a size of approximately 3000 nm, obtained from Invitrogen AB, Lidingö, Sweden. The particles were positively charged Amididine latex beads with a size of 3.5±0.29 μm (density 1.055 g/cm$^3$, surface area 1.7×10$^4$ cm/g), positively charged Aliphatic amine latex beads with a size of 2.9±0.12 μm (density 1.055 g/cm$^3$, surface area 2.0×10$^4$ cm/g), negatively charged CML latex beads with a size of 3.0±0.09 μm (density 1.055 g/cm$^3$, surface area 1.9×10$^4$ cm/g), and neutral (non-charged) non-ionic beads with a size of 3.1±0.06 μm (density 1.055 g/cm$^3$, surface area 1.8×10$^4$ cm/g).

Dextran particles, highly cross-linked agarose with dextran surface extender (Capto S and Capto Q) were obtained from GE Healthcare, Uppsala, Sweden. Capto S, strong cation ($SO_3^-$) with a particle size of 90 μm and Capto Q, strong anion ($N^+ (CH_3)$) with a particle size of 90 μm. Non-charged dextran particles of comparable size were used as control particles.

EXAMPLES

Three different categories of examples were carried out: in the A section, the technical equipment of the DETOL fluid or aerosol filter was tested and evaluated for its purpose; in the B section, the binding of virus in liquid and air by charged filter networks was evaluated; and in the C section, particles of various size and charge were tested in liquid and air for their ability to bind virus and negatively charged particles simulating virus.

A. Fluid or Aerosol Filter—Technical Equipment

Example 1

In this example the air flows in different parts of the technical equipment were determined. Capacity of the used fluid filter can be varied by the capacity of the cyclone (2, FIG. 1). In the hereby presented examples a low air flow corresponding to 0.009 m$^3$/s has been used and was measured by Veloci-Calc® Plus Multi-Parameter Ventilation Meter TSI 9555 from TSI Incorporated, USA.

Results: The air flow was high and similar in the various parts of the technical equipment (=fluid filter chamber), i.e. at the inlet (0.010 m$^3$/s), in the various parts of the fluid filter chamber (bottom center of the chamber: 0.010 m$^3$/s; middle center of the chamber: 0.009 m$^3$/s), and in the outlet of clean air (0.009 m$^3$/s). The measurements of airflow at above-mentioned positions were approximately 90 to 100% of the incoming air flow of 0.01 m$^3$/s as measured at the inlet.

Conclusion: There is very little reduction in airflow throughout the equipment. Also, the air is evenly distributed in the fluid filter chamber. Thus, the resistance of the curtain for the air to flow through the equipment was negligible.

Example 2

In this example the air flow, air turbulence and humidity were analysed in various parts of the technical equipment. These parameters were measured at the inlet, outlet as well as at various points through holes into the equipment when it was running under normal working conditions (FIG. 1a). The VelociCalc 9555 multi-function ventilation meter (TSI Instruments Ltd, USA) was used for carrying out the measurements.

Results: Air flow velocity through fluid filter was turbulent but homogenous in the different sections of the fluid filter chamber, i.e. 0.009 to 0.010 m$^3$/s. The humidity increased from the inlet to the outlet by 3%. The highest humidity was recorded above the fluid surface in the collection chamber for fluid and particles. At the other various points inside the fluid filter chamber the humidity was similar to the humidity in ambient environment measured at the inlet (FIG. 2).

Conclusion: Air flow was turbulent but homogenous at the inlet, outlet as well as at the various points of the equipment. The air humidity did not increase as the air passed through the technical equipment. The use of a cyclone removes particles or droplets of water and reduces humidity. The equipment can readily be complemented with a cooling system to reduce the total humidity or reversed be supplemented with humidifiers to satisfy comfort environment.

Example 3

In this example it was tested whether the technical equipment could efficiently clean the air from air-borne particles passing through the fluid filter chamber. Commercially available smoke (PURE-AX 9, 40032 with low chloride content, obtained from Björnax AB) was used. Content of smoke cartridges (smoke colour: white; size: 32×Ø18 mm.) was 9 g/cartridge. Smoke volume that developed from one cartridge was 8.5 m$^3$ during a burning time of 65 sec.

Results: It was shown that even particles in smoke were retrieved in the fluid filter collection chamber and also that the out-coming air that had passed through the fluid filter was visibly clean from small particles.

Conclusion: The fluid filter efficiently cleaned air from air-borne particles as generated by smoke cartridges. The use of a cyclone removes remaining particles that may have passed through the DETOL fluid or aerosol filter. Thus, the smoke creating an aerosol of dry particles support the claim that the DETOL fluid or aerosol filter will remove dry charged particles.

Example 4

In this example it was tested whether relatively large non-charged dextran particles could be kept in recirculation in the fluid filter system. A 4% suspension of 90 μm dextran particles in distilled water was used.

Results: The test with the non-charged dextran particles showed that even heavy particles of a size of 90 μm could be kept in recirculation without any noticeable sedimentation or problems with clotting in the nozzles.

Conclusion: Dextran particles in suspension could be recirculated and maintained as a fluid filter in the chamber of the technical equipment. The collection/recollection chamber to keep heavier particles in suspension by a shaker or by pressure waves.

Example 5

In this example it was tested whether relatively large positively (Capto Q) or negatively (Capto S) charged dextran particles could be kept in recirculation in the fluid filter system. A 4 percent suspension of 90 μm dextran particles (Capto Q and Capto S) in distilled water was used.

Results: The test with positively and negatively charged dextran particles showed that even charged heavy particles of a size of 90 μm could be kept in recirculation without any noticeable sedimentation or problems with clotting in the nozzles.

Conclusion: Dextran particles in suspension could be recirculated and maintained as a fluid filter in the chamber of the technical equipment.

General conclusion: By the technical equipment a fluid filter was produced that had high capacity, low resistance to the air and only a negligible increase in the humidity of the filtered air was observed.

B. Electrostatically Charged Cellulose Filter Networks

Example 6

In this example it was evaluated whether positively charged cellulose filter meshes attract and bind negatively charged virus in liquid. Conventional cellulose filters with a lipophilic character were tested, as well as cellulose filters covered by positively charged Quab molecules. The mesh size of the networks was approximately 1 mm. The strength of the binding was then tested by elusion with buffers of different ionic strength and pH.

Results: 80% of $^{35}$S-labelled coronavirus in a water solution was strongly bound by the positively charged filter. A substantial capture of virus occurred even though the electrostatic attraction for movement is much less in liquid than in air. In addition, the size of the filter mesh network is incredibly large compared to the size of the virus.

Conclusion: Virus in liquid bind firmly to positively charged cellulose filters. Notably, this efficient binding occurred despite the fact that the coronavirus being a membrane virus requiring to be kept in salt solution (in order not to be destroyed), where electrostatic movement is hampered.

Example 7

In this example it was evaluated whether positively charged cellulose filter meshes bind negatively charged virus in air. The charged filter concept (see example 6) was tested with airborne viruses, produced by aerosol generation of virus in water.

Results: When virus particles "in aerosol" were passed through the filter, significantly more (at least 2-fold) virus particles were repeatedly (in 5 experiments) caught by one single layer of the charged filter following a single passage compared to a passage through an uncharged filter.

Conclusion: Virus in air are attracted and bind to charged cellulose filters.

General conclusion: Positively charged hydrophobic cellulose filter networks efficiently bound negatively charged viruses in liquid and in air.

C. Particles

Example 8

In this example small positively charged particles were used to test the binding capacity of negatively charged viruses in liquid. Positively charged 3 μm Amidine latex particles (see Materials and Methods section) were tested in order to show whether they bind $^{35}$S-labelled coronavirus in water solution. In addition, negatively charged and non-charged particles were tested for proof of concept that only positively charged particles bind negatively charged viruses.

Results: Positively charged particles were shown to bind virus 23 times more efficiently than did non-charged beads. Non-charged latex particles did not bind detectable amounts of viruses. A further support of our concept is the fact that negatively charged latex beads did not bind negatively charged virus.

Conclusion: Positively charged small particles bind negatively charged viruses proving its suitability for capturing viruses.

Example 9

In this example large positively charged particles were used to test the binding capacity of negatively charged viruses in liquid. Positively charged 90 μm dextran Capto Q particles (see Materials and Methods section) were tested in order to show whether they bind $^{35}$S-labelled coronavirus in water solution. In addition, negatively charged and non-charged particles were tested for proof of concept that only positively charged particles bind negatively charged viruses.

Results: The positively charged 90 μm dextran particles were shown to efficiently bind $^{35}$S-labelled coronavirus in water solution. Non-charged dextran particles did not bind any amount of viruses. A further support of our concept is the fact that negatively charged dextran Capto S particles did not bind negatively charged virus.

Conclusion: Positively charged large particles bind negatively charged viruses and can be kept in circulation.

Example 10

In this example large positively charged particles were used to test the binding capacity of negatively charged particles simulating viruses in air. The capacity of the fluid filter, by the use large (90 μm) agarose Capto Q particles, to bind negatively charged particles in the size range of 0.10-3.00 μm (see Materials and Methods) was tested. Negatively charged particles simulating viruses in aerosol were created and passed through the fluid filter.

Results: Positively charged agarose Capto Q particles in the liquid curtain of the fluid filter reduced the amount of air-borne negatively charged particles. The degree of separation (%) varied depending on the sizes of the negatively charged particles, i.e. from 16±3 (0.10-0.12 μm) to 100±1 (2.00-3.00 μm). Particles in the size range of viruses (0.1-0.45 μm) were bound, supporting the concept that positively charged particles in the fluid filter system efficiently bind negatively charged air-borne virus.

Conclusion: Fluid filter with large positively charged particles bind negatively charged particles simulating negatively charged viruses.

General conclusion: Both small and large positively charged particles bound viruses, or particles simulating viruses, in liquid and in air and can be kept in circulation in the DETOL fluid and aerosol filter system.

Example 11

In this example, the equipment was tested with positively charged commercially obtained latex beads (3.5 μm particles) to capture negatively charged poly dispersed latex beads (particles) to mimic negatively charged pathogens e.g. viruses. The aim was to get a proof of concept regarding the device of equipment, capturing particles and the air streams, which is necessary information for designing subsequent experiments and for optimizing the particle device(s) and the equipment including components like nozzles, their shape(s), pumps creating pressure for the particle streams, sizes of capturing particles.

Materials and Methods: Particles mimicking pathogens (e.g. viruses) of various sizes i.e. poly disperse particles were negatively charged by an electronic aerosol neutralizer (Topas, EAN 580, aerosol neutralizer) by aid of a nozzle or an aerosol of indoor air. The aerosol concentrations were measured by an optical particle counter (0.1-3.0 μm) every second time upstream and downstream. Temperature and relative humidity was measured upstream and downstream.

Results: Proof of concept is shown in that virtually all of the particles of the sizes down to 0.5 μm are captured and removed from the treated air. Such particles are down to smaller sizes than bacteria. Even particles down to 0.2 μm, being the size of a virus, are to a certain degree captured, see the following Table. To note the equipment is an early prototype to be continuously developed according to the continuous experience being gained.

Discussion and Conclusion: This experiment demonstrates that the equipment and the particle device is a functioning concept. Particles smaller than the sizes of bacteria are efficiently captured and particles of the sizes of virus are captured to a limited extent. To note a virus particle has virtually no weight compared to a latex particle and will therefore be considerably more influenced by electrostatic attraction as demonstrated in example 7 where mm meshes attracted and captured virus with more than a million fold lower diameter. This example shows that the concept and the device have bearings. There is a complex of parameters that has to be adjusted for the final design of equipment and fluid filter components to complete the system for its final efficient use. A number of components and functions have to be adjusted based on practical development work including size(s) of capturing particles, their optimal or limiting charge for optimal capture capacity, density of capturing particles but not limited to these practical development work leading to experience that cannot be calculated from theoretical calculations. Pressure and speed for creations of curtains etc. are other parameters that can only be optimized by experience from practical work. This type practical development work is obvious for any person skilled in the field of optimizing inventions and particularly in the field of decontaminating and cleaning air. To note in a similar experiment indoor air, that normally contains mainly negatively charged particles of various sizes was tested and showed a similar capturing size profile. Thus, the experiment with indoor air particles being a dry aerosol support the claim that the equipment with the capturing particles used will capture dry particles in aerosol form as I also demonstrated in the example 3.

In conclusion, the concept of the invention has been proven based on a device including equipment forming continuous air flow curtains based on particles.

TABLE

The capturing capacity of the DETOL fluid or aerosol filter together with the positively charged 0.3 μm latex particles

| Particle size (μm) | | Particle capturing |
|---|---|---|
| Interval | Average | capacity (%) |
| 0.10-0.12 | 0.11 | 14 ± 6 |
| 0.12-0.15 | 0.13 | 17 ± 4 |
| 0.15-0.20 | 0.17 | 17 ± 5 |
| 0.20-0.25 | 0.22 | 26 ± 6 |
| 0.25-0.35 | 0.30 | 36 ± 2 |
| 0.35-0.45 | 0.40 | 53 ± 5 |
| 0.45-0.60 | 0.52 | 74 ± 4 |
| 0.60-0.75 | 0.67 | 94 ± 3 |
| 0.75-1.00 | 0.87 | 96 ± 2 |
| 1.00-1.50 | 1.22 | 98 ± 2 |
| 1.50-2.00 | 1.73 | 100 ± 0 |
| 2.00-3.00 | 2.45 | 100 ± 0 |

General conclusion: Both small and large positively charged particle bound viruses, or particles simulating viruses, in liquid and in air, can be kept in circulation in the DETOL fluid and aerosol filter system.

The invention claimed is:

1. A method for capturing airborne agents or products of agents, said airborne agents or products of agents being selected from the group consisting of microorganisms, viruses, microbial antigens, toxins, allergens and harmful and potentially harmful molecules, comprising: forming at least one curtain in air of stably charged particles, said particles being in the form of an emulsion of lipid-containing particles, or micelles, or an aerosol of dry particles, constantly renewing and regenerating said at least one curtain, and passing air containing said airborne agents or products of agents through said at least one curtain, and capturing said airborne agents or products of agents having an opposite charge.

2. The method according to claim 1, wherein said particles are collected and the captured airborne agents or products of agents are killed, and/or rendered harmless, respectively, and subsequently said particles are recirculated.

3. The method according to claim 2, wherein said particles are regenerated before recirculation.

4. The method according to claim 1, wherein said charged particles consist of built up polymers.

5. The method according to claim 1, wherein said charged particles consist of latex particles.

* * * * *